United States Patent [19]
Zimmermann et al.

[11] Patent Number: 5,997,863
[45] Date of Patent: *Dec. 7, 1999

[54] ATTENUATION OF WOUND HEALING PROCESSES

[75] Inventors: Joseph Zimmermann, Elm Grove, Wis.; Israel Vlodavsky, Jerusalem, Israel; Clark Bennett, Pierrefonds, Canada; Pamela Danagher; Richard Broughton, both of Montreal, Canada

[73] Assignee: Ibex Technologies R and D, Inc., Montreal, Canada

[21] Appl. No.: 08/273,109

[22] Filed: Jul. 8, 1994

[51] Int. Cl.⁶ .......................... A61K 38/51; A61K 38/47; C12N 9/88; C12N 9/26
[52] U.S. Cl. .................... 424/94.5; 424/94.61; 435/200; 435/201; 435/232; 514/2; 514/8; 530/825; 536/23.2; 536/23.4
[58] Field of Search ............................. 424/94.61, 94.5; 435/201, 850, 200, 232; 514/2, 8; 530/825; 536/23.2, 23.4

[56] References Cited

U.S. PATENT DOCUMENTS

| | | |
|---|---|---|
| 4,760,131 | 7/1988 | Sundsmo et al. . |
| 5,116,615 | 5/1992 | Gokcen et al. . |
| 5,169,772 | 12/1992 | Zimmermann et al. ................. 435/232 |
| 5,242,810 | 9/1993 | Maraganore et al. . |
| 5,262,325 | 11/1993 | Zimmermann et al. ................. 435/269 |
| 5,362,641 | 11/1994 | Fuks et al. . |
| 5,389,539 | 2/1995 | Sasisekharan et al. . |

FOREIGN PATENT DOCUMENTS

PCT US90/06590  5/1991  WIPO .

OTHER PUBLICATIONS

Silver, P. (1988) IBT 9302 (Heparinase III): a novel enzyme for the management of reperfusion injury–related vascular damage, restinosis and wound healing. Exp. Opin. Invest. Drugs 7(6):1003–1014.

Ernst et al. (1995) Enzymatic Degradation of Glycosaminoglycans. Crit. Rev. Biochem. Mol. Biol. 30(5): 387–444.

Baird and Klagsbrun, "The Fibroblast Growth Factor Family," Ann. N.Y. Acad. Sci. 638:x1 (1991).

Bashkin et al., "Release of Cell Surface–Associated Basic Fibroblast Growth Factor by Glycosyiphosphatidylinositol–Specific Phospholipase C," J. Cell. Physiol. 157:126–137 (1992).

Bohn, et al., "Fragmentation of Heparin by Enzymes from Newly Isolated Microorganisms," Drug Res. 41(1), Nr. 4:456–460 (1991).

Burgess and Macaig, "The Heparin–Binding (Fibroblast) Growth Factor Family of Proteins," Ann. Rev. Biochem, 58:575–606 (1989).

Clark, "Biology of Dermal Wound Repair," Dermatol. Clin. 11:647–666 (1993).

Cohen et al., "Nonchromosomal Antibiotic Resistance in Bacteria: Genetic Transformation of Escherichia coli by R–Factor DNA," Proc. Natl. Acad. Sci. 69:2110–211 (1972).

Delgado, et al., "The Uses and Properties of PEG–Linked Proteins," Critical Rev. Ther. Drug Carrier Syst. 9(3–4):249–304 (1992).

Desai, et al., "Substrate Specificity of the Heparin Lyases from Flavobacterim heparinum," Arch. Biochem. Biophys. 306:461–468 (1993).

Folkman and Klagsbrun, "Angiogenic Factors," Science 235:442–447 (1987).

Folkman, et al., "A Heparin–Binding Angiogenic Protein–asic Fibroblast Growth Factor–Is Stored Within Basement Membrane," Am J Pathol 130:393–400 (1988).

Folkman and Shing, "Angiogenesis," J. Biol. Chem. 267(16):10931–10934 (1992).

Gaal et al., "Retina contains endogenous heparinase activity," Biochem. Biophys. Res. Comm., 161:604–614 (1989).

Galliher et al., "Heparinase Production by Flavobacterium heparinum," Appl Environ. Microbiol. 41(2):360–365 (1981).

Higashiyama, et. al., "A Heparin–Binding Growth Factor Secreted by Macrophage–Like Cells That Is Related to EGF," Science 251:936–939 (1991).

Hiyam and Okada, "Crystallization and Some Properties of Chondroitinase from Arthrobacter aurescens," J. Biol. Chem. 250:1824–1828 (1975).

Kirsner and Eaglstein, "The Wound Healing Process," J. Dermatol. 151:629–640 (1993).

Kitamikada and Lee, "Chondrotinase–Producing Bacteria in Natural Habitats," Appl. Microbiol. 29:414 (1975).

(List continued on next page.)

Primary Examiner—Lisa J. Hobbs
Attorney, Agent, or Firm—Arnall Golden & Gregory, LLP

[57] ABSTRACT

Glycosaminoglycans, including heparinases 1, 2 and 3 as well as chondroitinases AC and B from the Gram negative bacteria Flavobacterium heparinum, can be used either separately or in combination to manipulate cell proliferation. In one embodiment, heparinases are administered to degrade heparan sulfate components of the extracellular matrix, thereby allowing the heparin binding growth factors which are stored in the extracellular matrix to migrate to adjacent cells. The mobility of chemoattractant agents, growth factors and cells also can be increased by treating tissues with glycosaminoglycan degrading enzymes, both chondroitinases and heparinases. The enzymatic removal of chondroitin sulfates from cell surfaces effectively increases the availability of growth factor receptors on the cell's surface. Selectively removing heparan sulfate from cell surfaces while leaving the extracellular matrix intact, conversely, inhibits cell proliferation by down regulating the cell's response to growth factors. This is achieved by targeting heparin or heparan sulfate degrading activities to the cell surface. Targeting the heparin degrading activity can be achieved by genetically engineering a ligand binding functionality into the heparinase proteins, or by physically controlling the localized enzyme concentration through the method of administration.

17 Claims, 4 Drawing Sheets

OTHER PUBLICATIONS

Linn, et al., "Isolation and Characterization of Two Chondroitin Lyases from *Bacteriodes thetaiotamicron*," *J. Bacteriol.* 156:859 (1983).

Lohse and Linhardt, "Purification and Characterization of Heparin Lyases from *Flavobacterium heparinum*," *J. Biol. Chem.* 267:24347–24355 (1992).

Lowell, et al., "Proteosome–Lipopeptide Vaccines: Enhancement of Immunogenicity for Malaria CS Peptides," Science, 240:800 (1988).

Lu, et al., "Pegylated Peptides I: Solid–Phase Synthesis of $N^\alpha$–Pegylated Peptides Using Fmoc Strategy," *Pept. Res.* 6(3), 140–146 (1993).

Michaleacci, et al., "A Comparative Study Between a Chondroitinase B and a Chondroitinase AC from *Flavobacterium heparinum*," *Biochem. J.* 151:123 (1975).

Miller et al., "Vaccination of Rhesus Monkeys with Synthetic Peptide in a Fusogenic Proteoliposomes Elicits Simian Immunodeficiency Virus–specific CD8+ Cytotoxic T Lymphocytes," *J. Exp. Med.* 176:1739–1744 (1992).

Nakajima, et al., "Metatastic Melanoma Cell Heparanase," *J. Biol. Chem.* 259:2283–2290 (1984).

Nakajima et al., "Heparanases and Tumor Metastasis," *J. Cell. Biochem.* 36:157–167 (1988).

Nakamura, et al., "Purification and Properties of *Bacteriodes heparinolyticus* Heparinase (Heparin Lyase EC 4.2.2.7)," *J. Clin. Microbiol.* 26:1070–1071 (1988).

Nathan and Sporn, "Cytokines in Context," *J. Cell Biol.* 113:981–986 (1991).

Nicolson, "Metastatic tumor cell interactions with endothelium, basement membrane and tissue," *Curr. Opinion Cell Biol.* 1:1009–1019 (1989).

Oldberg et al., "Characterization of a Platelet Endoglycosidase Degrading Heparin–like Polysaccharides," *Biochemistry* 19:5755–5762 (1980).

Pickering, et al., "Prevention of Smooth Muscle Cell Outgrowth from Human Atherosclerotic Plaque by a Recombinant Cytotoxin Specific for the Epidermal Growth Factor Receptor," *J. Clin Invest*, 91:724–729 (1993).

Pu, et al., "Enhanced Revascularization of the Ischemic Limb by Angiogenic Therapy," *Circulation* 88:208–215 (1993).

Sasisekharan, et al., "Cloning and expression of heparinase I gene from *Flavobacterium heparinum*," *Proc. Natl. Acad. Sci.* 90:3660–3664 (1993).

Savlers, et al., "Induction of Chondroitin Sulfate Lyase Activity in *Bacteriodes thetaiotaomicron*," *J. Bacteriol.* 143:781 (1980).

Saylers, et al., "Fermentation of Mucin and Plant Polysaccharides by Strains of Bacteroides from the Human Colon," *Appl. Environ. Microbiol.* 33:319–322 (1977).

Staiano–Coico, et al., "Human Keratinocyte Growth Factor Effects in a Porcine Model of Epidermal Wound Healing," *J. Exp. Med.* 178:865–878 (1993).

Steffen, et al., "Hydrolytic Enzymes of Anaerobic Bacteria Isolated from Human Infections," *J. Clin. Microbiol.*, 14:153 (1981).

Suzuki, "Chondroitinases from *Proteus vulgaris* and *Flavobacterium heparinum*," *Meth. Enzymol.* 28:911 (1972).

Turnbull, et al., "Identification of the Basic Fibroblast Growth Factor Binding Sequence in Fibroblast Heparan Sulfate," *J. Biol. Chem.* 267(15) 10337–10341 (1992).

Uamagata, et al., "Purification and Properties of Bacterial Chondroitnases and Chondrosulfatases," *J. Biol. Chem.* 243:1523 (1968).

Vlodavsky et al., "Endothelial cell–derived basic fibroblast growth factor: Synthesis and deposition into subendothelial extracellular matrix," *Proc. Natl. Acad. Sci.* 84:2292–2296 (1987).

Vlodavsky et al., "Extracellular sequestration and release of fibroblast growth factor: a regulatory mechanism," *TIBS* 16:268:271 (1991).

Werner, et al., "Large induction of keratinocyte growth factor expression in the dermis during wound healing" *Proc. Natl. Acad. Sci.* 89:6896 (1992).

Yang, et al., "Purification and Characterization of Heparinase from *Flavobacterium heparinum*," *J. Biol. Chem.* 260(3):1849–1857 (1985).

Yavon, et al., "Cell Surface, Heparin–like Molecules Are Required for Binding of Basic Fibroblast Growth Factor to its High Affinity Receptor," *Cell* 64:841–848 (1991).

Zimmermann, et al., "Specific Plate Assay for Bacterial Heparinase," *Appl. Environ. Microbiol.* 56(11):3593–3594 (1990).

Yoshida, et al., 10th International Symposium On Glycoconjugates Proceedings, pp. 330–331 (Sep. 10–15, 1989).

Sasisekharan et al 1994 PNAS USA 91:1524–1528.

Sasisekharan et al 1993 PNAS USA 90:3660–3664.

ATTENUATION OF WOUND HEALING PROCESSES

BACKGROUND OF THE INVENTION

The present invention describes a methodology for the use of glycosaminoglycan degrading enzymes to modulate events in the wound healing process.

Growth factors are naturally occurring polypeptides that elicit hormone type modulation of cell proliferation and differentiation. The mechanism by which these events transpire is typically initiated by the growth factor contacting specific receptors or receptor systems which are located on the cell surface. The sequence of intracellular events that occur subsequent to the receptor/growth factor interaction are responsible for mitogenic and differentiating responses by the cell. These mechanisms are not fully understood but may include activation of tyrosine kinases, nucleotide metabolism and variations in cell electrolyte levels (Burgess and Macaig, *Ann. Rev. Biochem*, 58:575–606, 1989).

For most cell types, events of mitogenesis and differentiation are subdued in the normal adult animal. These growth factor mediated events are more commonly associated with developing organisms, during wound healing processes or in various disease states including cancer and vascular disease. For example, the normal turnover rate of endothelial cells, including the lining of microvessels and arteries, is measured in thousands of days. During normal wound healing however, these endothelial cells proliferate rapidly, with a turnover rate of approximately five days (Folkman and Shing, *J. Biol. Chem.* 267(16):10931–10934, 1992). The increase in proliferation that occurs during wound healing appears to be the result of an increase in the local concentration of various angiogenic molecules, including growth factors.

The fibroblast growth factor family includes at least seven polypeptides that have been shown to stimulate proliferation in various cell lines including endothelial cells, fibroblasts, smooth muscle cells and epidermal cells. Included in this group are acidic fibroblast growth factor (FGF-1), basic fibroblast growth factor (FGF-2), int-2 (FGF-3), Kaposi sarcoma growth factor (FGF-4), hst-1 (FGF-5), hst-2 (FGF-6) and keratinocyte growth factor; (FGF-7) (Baird and Klagsbrun, *Ann. N.Y. Acad. Sci.* 638: xiv, 1991). These molecules, and other cytokines including tissue growth factors, TGFα and TGFβ, platelet derived growth factors, PDGF, granulocyte-macrophage colony stimulating factor, GM-CSF, interleukin 3, IL-3, and platelet factor 4, PF4, share a common feature in their affinity for heparin (Clark, *Dermatol. Clin.* 11:647–666, 1993). Specific cell type responses also have been associated with particular factors. EGF and TGFα stimulate the proliferation of keratinocytes, TGFβ stimulates collagen and fibronectin synthesis, PDGF stimulates angiogenesis and granulation tissue formation and FGF-7 stimulates epithelial cell proliferation (Staiano-Coico, et al., *J. Exp. Med.* 178:865–878, 1993). PDGF, FGF-2 and a recently described heparin binding epidermal growth factor HB-EGF (Higashiyama, et. al., *Science* 251:936–939, 1991) additionally are involved in the proliferation and migration of vascular smooth muscle cells and vascular endothelial cells.

The change in a cell's metabolic state from quiescent to proliferative or migratory implies an enhanced availability of the appropriate signaling molecules in the vicinity of the cell. In principle this could result from either an increase in growth factor synthesis or the release of growth factors from storage reservoirs. In nature, both mechanisms have been observed. The expression of FGF-1, FGF-2, FGF-5 and FGF-7 are upregulated after full thickness dermal injury (Werner, et. al., *Proc. Natl. Acad. Sci.* 89:6896) while TGFβ, FGF-2 and PDGF synthesis increases in smooth muscle cells in response to vascular injury. Growth factors also have been detected in most solid tissues extracted from normal adult, non-wounded samples. Despite the presence of growth factors in these areas, the cells comprising them are not in a proliferative state. Apparently, growth factors are stored outside the cell in basement membranes and the extracellular matrix where they are prevented from contacting their respective cell surface receptors. In this mode they serve as an emergency supply for wound repair and blood vessel formation functions (Vlodavsky, et. al. *TIBS* 16:268–271, 1991).

An initial event in tissue or vessel injury may involve a mechanical dislodging of growth factors from the extracellular space, making them available to cell surface receptors where they stimulate cell proliferation and cell synthesis of additional growth factors. Alternately, cells under stress may secrete molecules which displace the extracellular growth factors from these storage reservoirs. Tumor cells have been shown to secrete degradative enzymes, including proteoglycanases, collagenases and metalloproteinases, coincident with metastasis (Nicolson *Curr. Opinion Cell Biol.* 1:1009–1019, 1989). In addition to facilitating tumor migration through blood vessels, the destruction of extracellular matrix components releases growth factors, thereby promoting new blood vessel formation which feeds the growing tumor mass (Folkman, et al., *Am J Pathol* 130:393–400, 1988).

Extracellular matrices (ECM) are multi-component structures synthesized by and surrounding various cell types including endothelial, epithelial, epidermal and muscle cells. The ECM is formed largely of collagen and heparan sulfate proteoglycans. It also contains fibronectin, chondroitin sulfate proteoglycans and smaller proteins. Growth factors are sequestered in these matrices by association with the glycosaminoglycan portion of the heparan sulfate proteoglycans. Heparin and heparan sulfate are polysaccharides formed of alternating hexuronic, either D-glucuronic or L-iduronic, and glucosamine, N-acetylated or N-sulfated, residues with varying sulfation patterns. Heparin extracted from porcine intestines, bovine lungs or human mast cells displays a high degree of sulfation, up to 2.6 sulfates per disaccharide unit, and a greater iduronic acid content than heparan sulfate. Conversely, heparan sulfate has a lower degree of sulfation and preferentially contains glucuronic acid in the alternating saccharide position. "Heparin like" regions of high iduronic acid and high sulfation have been associated with the bFGF binding region of heparan sulfate from human fibroblasts (Turnbull, et al., *J. Biol. Chem.* 267(15) 10337–10341, 1992). However, the composition of heparan sulfate in the extracellular matrix has not been fully characterized.

The stimulation of cell proliferation and migration by growth factors constitutes one of the events in the wound healing process which is a multifactoral interactive process involving biochemical mediators, the extracellular matrix and parenchymal cells. The wound healing process is generally divided into three temporally overlapping phases: inflammation, proliferation and remodeling. During inflammation, blood borne cells infiltrate the wound site and release several mediating molecules including platelet derived growth factor, von Willibrand factor, thrombospondin, fibronectin, fibrinogen, 5-hydroxytryptophan, thromboxane-A2 and adenosine diphosphate (Kirsner and Eaglstein, *J. Dermatol.* 151:629–640, 1993). A platelet plug and thrombus are formed and provide a matrix for monocytes, fibroblasts and keratinocytes. Chemotactic molecules attract monocytes which transform into macrophages and secrete additional growth factors (Nathan and Sporn, *J. Cell Biol.* 113:981–986, 1991). Neutrophils may assist in this process by secreting the degradative enzymes elastase and collagenase which enhance the passage of cells through the basement membranes.

Keratinocytes and epidermal cells, which are involved in the closure of dermal wounds, migrate to the wound site during the proliferative phase. Angiogenesis, the formation of new blood vessels in response to chemoattractant and angiogenic signals (Folkman and Klagsbrun, *Science* 235:442–447, 1987), and fibroplasia, the accumulation of fibroblasts and formation of granulation tissue, also occurs during the proliferative phase. Tissue remodeling is accompanied by the secretion of matrix components, including fibronectin, collagen and proteoglycans which serve as a scaffold for cellular migration and tissue support. Type III collagen, synthesized in the earlier stages of wound healing, is replaced by the more permanent type I form through a process of proteolytic turnover.

Ischemia refers to the pathological condition due to the localized dysfunction of the vascular system resulting in inadequate blood supply with subsequent tissue damage. In this case revascularization, whether through the stimulation of angiogenesis or by surgical methods, must precede the normal wound healing course of the damaged tissue.

The action of enzymes which degrade components of the extracellular matrix and basement membranes may facilitate the events of tissue repair by a variety of mechanisms including the release of bound cytokines entrapped by heparan sulfate and by increasing the permeability of the matrix, thereby enhancing the mobility of mediator molecules, growth factors and chemotactic agents, as well as the cells involved in the healing process. Glycosaminoglycans are subject to degradation by a variety of eukaryotic and prokaryotic enzymes. Heparan sulfate degrading activity has been detected in platelets (oldberg et al. *Biochemistry*, 19:5755–5762, 1980), tumor cells (Nakajima, et al. *J. Biol. Chem.* 259:2283–2290, 1984) and endothelial cells (Gaal et al. *Biochem. Biophys. Res. Comm.*, 161:604–614, 1989). These heparanase enzymes act by catalyzing the hydrolysis of the carbohydrate backbone of heparan sulfate at the hexuronic acid (1→4) glucosamine linkage (Nakajima et al., *J. Cell, Biochem.*, 36:157–167, 1988). Mammalian heparanases are typically inhibited by the highly sulfated heparin form of the heparin-heparan sulfate family. However, accurate biochemical characterizations of these enzymes have thus far been prevented by the lack of a method to obtain homogeneous preparations of the molecules.

Heparin degrading enzymes also have been found in microorganisms including *Flavobacterium heparinum* (Lohse and Linhardt, *J. Biol. Chem.* 267:2437–24355, 1992), Bacteroides strains (Saylers, et al., *Appl. Environ. Microbiol.* 33:319–322, 1977; Nakamura, et al., *J. Clin. Microbiol.* 26:1070–1071, 1988), Flavobacterium Hp206 (Yoshida, et al., 10th Annual Symposium of Glycoconjugates, Jerusalem 1989) and Cytophagia species (Bohn, et al., *Drug Res.* 41(I), Nr. 4:456–460, 1991). Chrondoitin sulfate degrading enzymes have been isolated from several microorganisms including *Flavobacterium heparinum* (Michaleacci, et al., *Biochem. J.* 151:123, 1975), Bacteroides species (Saylers, et al. *J. Bacteriol.* 143:781, 1980; Linn, et al., *J. Bacteriol.* 156:859, 1983; Steffen, et al., *J. Clin. Microbiol.* 14:153, 1981), Proteus vulgaris (Uamagata, et al., *J. Biol. Chem.* 243:1523, 1968, Suzuki, *Meth. Enzymol.* 28:911, 1972), Beneckea, Microcossus and Vibrio species (Kitamikada and Lee, *Appl. Microbiol.* 29:414, 1975) and *Arthrobacter aurescens* (Hiyam and Okada, J. Biol. Chem. 250:1824–1828, 1975).

*F. heparinum* produces three forms of heparinase, heparinase 1, heparinase 2, and heparinase 3 (heparitinase) (Lohse and Linhardt, *J. Biol. Chem.* 267:24347–24355, 1992). All three enzymes cleave at glucosamine (1→4) hexuronic acid linkages with differing degrees of specificity depending on sulfation patterns and particular hexuronic acid residue, iduronic or glucuronic, in a particular cleavage site (Desai, et al., *Arch. Biochem. Biophys.* 306:461–468, 1993). *F. heparinum* also produces two enzymes which degrade members of the chondroitin sulfate/dermatan sulfate family. These are chondroitin lyase AC, which degrades both chondroitin sulfate A and chondroitin sulfate C by cleaving the galactosamine (1→4) glucuronic acid linkage in the polysaccharide backbone and chondroitin lyase B which degrades dermatan sulfate (chondroitin sulfate B) by cleaving the galactosamine (1→4) iduronic acid linkage in the polysaccharide backbone. The enzymatic mechanism of the *F. heparinum* enzymes is through an elimination reaction, thereby differentiating them from the mammalian glycosaminoglycan degrading enzymes. Furthermore, none of the *F. heparinum* lyase enzymes appear inhibited by glycosaminoglycan molecules as are the mammalian enzymes.

Mammalian heparanase, partially purified from tumor cell line extracts, as well as heparinase 1 and heparinase 3 from *Flavobacterium heparinum*, have been shown to release $^{125}$I radiolabelled FGF-2 that had been pre-adsorbed to extracellular matrix synthesized in vitro by bovine aorta endothelial cells (Bashkin, et al. *J. Cell. Physiol.* 167:126–137, 1992). However, since unfractionated and low molecular weight heparin elicited a similar release of the exogenously absorbed $^{125}$I radiolabelled FGF-2, it is not clear from these reports whether the measured release was due to the enzymatic degradation of the heparan sulfate in the ECM or an ion exchange type electrolytic displacement of FGF-2 from the negatively charged heparan sulfate. The same research group reported the release of growth promoting activity from vascular smooth muscle cells by treatment with heparinase 3 and from extracellular matrix by exposure to extracts of neutrophils or lymphoma cells. However, there has been no demonstration of the release of growth promoting activity from extracellular matrix by contact with bacterial glycosaminoglycan degrading enzymes nor have these enzymes been shown to promote tissue repair or new vessel growth in vivo.

It is therefore an object of the present invention to provide a method and compositions for enhancing and controlling tissue repair and new vessel growth.

It is a further object of the present invention to provide highly purified glycosaminoglycan degrading enzyme pharmaceutical compositions for use in enhancement of tissue repair and manipulation of angiogenesis.

SUMMARY OF THE INVENTION

Glycosaminoglycans, including heparinases 1, 2 and 3 as well as chondroitinases AC and B from the Gram negative bacterium *Flavobacterium heparinum*, can be used either separately or in combination to manipulate cell proliferation. In one embodiment, heparinases are administered to degrade heparan sulfate components of the extracellular matrix, thereby allowing the heparin binding growth factors which are stored in the extracellular matrix to migrate to adjacent cells. The mobility of chemoattractant agents, growth factors and cells can also be increased by treating tissues with glycosaminoglycan degrading enzymes, both chondroitinases and heparinases. The enzymatic removal of chondroitin sulfates from cell surfaces effectively increases the availability of growth factor receptors on the cell's surface. Selectively removing heparan sulfate from cell surfaces while leaving the extracellular matrix intact, conversely, inhibits cell proliferation by down regulating the cell's response to growth factors. This is achieved by targeting heparin or heparan sulfate degrading activities to the cell surface. Targeting the heparin degrading activity can be achieved by genetically engineering a ligand binding functionality into the heparinase proteins, or by physically controlling the localized enzyme concentration through the method of administration.

Methods for preparing glycosaminoglycan enzymes and genetically engineered derivatives of them as well as methods for producing pharmaceutical preparations of highly purified glycosaminoglycan degrading enzymes are described. Methods are disclosed to produce derivatives of the heparin degrading enzymes which incorporate binding properties of other proteins. These molecules can be used to target the heparin degrading activity to the cell surface which inhibit a cell's response to endogenous growth factors.

BRIEF DESCRIPTION OF THE DRAWINGS

FIGS. 1*a*, 1*b*, and 1*c* are schematic diagrams depicting the function of glycosaminoglycans in the extracellular matrix (ECM—top half) and on cell surfaces (bottom half). FIG. 1*a* shows that the heparan sulfate component (plain squiggled line) of heparan sulfate proteoglycans (HSPG) binds to heparin binding growth factors (HBGF) in both the extracellular matrix and at the cell surface. Growth factors not bound to heparan sulfate are unable to bind their cell surface receptor. Heparan sulfate or fragments of heparan sulfate attach to the growth factors and elicit a conformational change which allows binding to the receptor. Chondroitin sulfate (hatched squiggled line) proteoglycans (CSPG) also are located in the extracellular matrix and on the cell surface. At the cell surface the chondroitin sulfate molecules may sterically hinder the access of heparin binding growth factor receptors. FIG. 1*b* shows that treatment with chondroitin sulfate degrading enzymes allows greater access to the cell surface receptors and increases the mobility of molecules such as chemoattractants, growth factors and cells through the extracellular matrix. FIG. 1*c* shows that treatment with heparin or heparan sulfate degrading enzymes releases heparan sulfate fragments and heparin binding growth factors from the extracellular matrix, thereby increasing their availability to the adjacent cell surface receptors, and increases the mobility of molecules such as chemoattractants, growth factors and cells through the extracellular matrix.

FIG. 2 is a graph of the desorption (penetration into agarose (mm) over time (minutes)) of heparinase into semisolid gels to measure the amount of enzyme present.

FIG. 3 is a graph of relative growth promoting activity released from enzyme treated extracellular matrix (x control) for untreated, heparinase 1, heparinase 2, heparinase 3, chondroitinase AC and chondroitinase B. The results are expressed as the ratio of thymidine incorporation by Balb/c 3T3 fibroblasts exposed to enzyme treated matrix supernatants to that of untreated matrix supernatants.

FIG. 4 is a graph of the relative growth promoting activity released from enzyme treated bovine corneas (x control) for untreated, heparinase 1, heparinase 2, and heparinase 3. The results are expressed as the ratio of thymidine incorporation by Balb/c 3T3 fibroblasts exposed to enzyme treated corneal supernatants to that of untreated corneal supernatants.

FIG. 5 is a graph of the release of $^{35}S$ from extracellular matrix (cpm) for untreated, heparinase 1, heparinase 2, heparinase 3, chondroitinase AC, and chondroitinase B.

FIG. 6 is a graph of the relative adsorption of FGF-2 by enzyme treated balb/C 3T3 fibroblasts (% of control) for untreated, heparinase 1, heparinase 2, and chondroitinase AC.

FIG. 7 is a graph of the relative proliferative response of Balb/C 3T3 fibroblasts to enzymatic treatment of either the cell surface, extracellular matrix or both. Proliferation was determined by $^3H$-thymidine incorporation and is expressed as the ratio of incorporation observed in the treated conditions to that of the control (untreated cells exposed to supernatant from untreated matrix).

DETAILED DESCRIPTION OF THE INVENTION

A methodology for controlling events involved in wound healing processes by the use of highly purified glycosaminoglycan degrading enzymes derived from *Flavobacterium heparinum* genes is disclosed. Glycosaminoglycans, including heparan sulfate, chondroitin sulfate and dermatan sulfate, are the sulfated polysaccharide components of proteoglycans located on cell surfaces, where they act as cytokine receptors and in the extracellular space where they form the structure of the extracellular matrix and serve as a storage reservoir for growth factors. Glycosaminoglycan degrading enzymes from *F. heparinum*: heparinase 1 (EC 4.2.2.7), heparinase 2, heparinase 3 (EC 4.2.2.8), chondroitinase AC (EC 4.2.2.5) and chondroitinase B modulate the interactions involved in cell proliferation and migration by i) releasing heparin binding growth factors and molecules from the extracellular matrix, thereby increasing their availability to adjacent cells for the stimulation of proliferation and migration, ii) degrading components of the extracellular matrix, thereby facilitating the mobility of cytokines, chemoattractants and cells, iii) removing chondroitin sulfate from cell surfaces, thereby increasing access to cell surface receptors and iv) inhibiting the proliferative response of cells to growth factors by removing the heparan sulfate component of their growth factor receptor complex.

Heparin binding growth factor-receptor interactions require the presence of a third component: heparan sulfate, which is present on cell surfaces, or can be added to the cells, or released lytically as a heparan sulfate fragment from the extracellular matrix. The addition of heparin or heparan sulfate degrading enzymes in the range of between 0.001 and 5 IU/ml promotes cell proliferation by co-releasing heparin binding growth factors and heparan sulfate fragments from the extracellular matrix and increasing their availability to adjacent cells.

Selectively removing heparan sulfate from cell surfaces while leaving the extracellular matrix intact, conversely, inhibits cell proliferation by down regulating the cell's response to growth factors. This is achieved by targeting heparin or heparan sulfate degrading activities to the cell surface. Targeting the heparin degrading activity can be achieved by genetically engineering a ligand binding functionality into the heparinase proteins, or by physically controlling the localized enzyme concentration through the method of administration. For example, permeable double balloon catheters can direct heparinases, preferentially, to exposed vascular smooth muscle cells in injured vessels.
Preparation of Glycosaminoglycan Degrading Enzymes D Glycosaminoglycan lysase enzymes can be prepared by isolation from bacterial or mammalian cells, either those which naturally produce the enzymes or have been genetically engineered to produce the enzymes.

Isolation of Naturally Produced Enzymes.

Glycosaminoglycan lyase enzymes can be purified from cultures of Flavobacterium heparinum, as follows. *F. heparinum* is cultured in 15 L computer controlled fermenters, in a variation of the defined nutrient medium described by Galliher et al., *Appl Environ. Microbiol.* 41(2):360–365, 1981. For fermentations designed to produce heparin lyases, semi-purified heparin (Celsus Laboratories) is included in the media at a concentration of 1.0 g/L as the inducer of heparinase synthesis. For fermentations designed to produce chondroitin lyases, chondroitin sulfate A (Sigma) is included in the media at a concentration of 1.0 g/L as the inducer of chondroitinase AC and chondroitinase B synthesis. For both types of fermentation, the cells are harvested by centrifugation and the desired enzymes released from the periplasmic space by a variation of the osmotic shock procedure described by U.S. Pat. No. 5,169,772 to Zimmermann, et al. (1992).

Proteins from the crude osmolate are adsorbed onto cation exchange resin (CBX, J. T. Baker) at a conductivity of between one and seven μmho. Unbound proteins from the extract are discarded and the resin packed into a chromatography column (5.0 cm i.d.×100 cm). The bound proteins elute at a linear flow rate of 3.75 cm·min$^{-1}$ with step gradients of 0.01 M phosphate, 0.01 M phosphate/0.1 M sodium chloride, 0.01 M phosphate/0.25 M sodium chloride and 0.01 M phosphate/1.0 M. sodium chloride, all at pH, 7.0±0.1. Heparinase 2 elutes in the 0.1 M NaCl fraction while heparinases 1 and 3 elute in the 0.25 M fraction. Alternately, the 0.1 M sodium chloride step is eliminated and the three heparinases co-eluted with 0.25 M sodium chloride. The heparinase fractions are loaded directly onto a column containing cellufine sulfate (5.0 cm i.d.×30 cm, Amicon) and eluted at a linear flow rate of 2.50 cm·min$^{-1}$ with step gradients of 0.01 M phosphate, 0.01 M phosphate/ 0.2 M sodium chloride, 0.01 M phosphate/0.4 M sodium chloride and 0.01 M phosphate/1.0 M. sodium chloride, all at pH, 7.0±0.1. Heparinase 2 and 3 elute in the 0.2 M sodium chloride fraction while heparinase 1 elutes in the 0.4 M fraction. The 0.2 M sodium chloride fraction from the cellufine sulfate column is diluted with 0.01 M sodium phosphate to give a conductance less than 5 μmhos. The solution is further purified by loading the material onto a hydroxylapatite column (2.6 cm i.d.×20 cm) and eluting the bound protein at a linear flow rate of 1.0 cm·min–1 with step gradients of 0.01 M phosphate, 0.01 M phosphate/0.35 M sodium chloride, 0.01 M phosphate/0.45 M sodium chloride, 0.01 M phosphate/0.65 M sodium chloride and 0.01 M phosphate/1.0 M. sodium chloride, all at pH, 7.0±0.1. Heparinase 3 elutes in a single protein peak in the 0.45 M sodium chloride fraction while heparinase 3 elutes in a single protein peak in the 0.65 M sodium chloride fraction. Heparinase 1 is further purified by loading material from the cellufine sulfate column, diluted to a conductivity less than 5 μmhos, onto a hydroxylapatite column (2.6 cm i.d.×20 cm) and eluting the bound protein at a linear flow rate of 1.0 cm·min–1 with a linear gradient of phosphate (0.01 to 0.25 M) and sodium chloride (0.0 to 0.5 M). Heparinase 1 elutes in a single protein peak approximately mid-way through the gradient.

The heparinase enzymes obtained by this method are greater than 98.5% pure as estimated by reverse phase HPLC analysis (BioCad, POROS II). Purification results for the heparinase enzymes are shown in Table 1.

TABLE 1

Purification of heparinase enzymes from *Flavobacterium heparinum* fermentations

| sample | activity (IU) | specific activity (IU/mg) | yield (%) |
|---|---|---|---|
| fermentation | | | |
| heparin degrading | 94,500 | | 100 |
| heparan sulfate degrading | 75,400 | ND | 100 |
| osmolate heparin degrading | 52,100 | | 55 |
| heparan sulfate degrading | 42,000 | ND | 56 |
| cation exchange | | | |
| heparin degrading | 22,600 | | 24 |
| heparan sulfate degrading | 27,540 | ND | 37 |
| cellufine sulfate | | | |
| heparin degrading | 19,200 | | 20 |
| heparan sulfate degrading | 9,328 | 30.8 | 12 |
| hydroxylapatite | | | |
| heparinase 1 | 16,300 | 115.3 | 17 |
| heparinase 2 | 2,049 | 28.41 | 3 |
| heparinase 3 | 5,150 | 44.46 | 7 |

Osmolates obtained from *F. heparinum* fermentations induced with chondroitin sulfate A are subjected to centrifugation to remove cells and cell debris and the supernatant applied to a cation exchange column (5.0 cm×30 cm, Sepharose™ S Big Beads, Pharmacia) at a linear flow rate of 10 cm·min$^{-1}$. The bound proteins are eluted at a linear flow rate of 5.1 cm·min$^{-1}$ with step gradients of 0.01 M phosphate, 0.01 M phosphate/0.25 M sodium chloride and 0.01 M phosphate/1.0 M. sodium chloride, all at pH, 7.0±0.1. Chondroitinase activity elutes in the 0.25 M sodium chloride fraction which is further purified by diluting the chondroitinase containing fraction two-fold with 0.01 M sodium phosphate and applying the material onto a column containing cellufine sulfate (2.6 cm i.d.×100 cm, Amicon) and eluting at a linear flow rate of 1.88 cm·min$^{-1}$ with a linear gradient of sodium chloride, 0.0 to 0.4 M. Chondroitinase AC primarily elutes at 0.23 to 0.26 M sodium chloride while chondroitinase B eluted at 0.27 to 0.3 M sodium chloride. Each fraction was diluted two-fold with 0.01 M sodium phosphate and applied to a hydroxylapatite column (2.6 cm i.d.×30 cm). The bound proteins are eluted with a step gradient of 0.25 M sodium chloride followed by a linear gradient of 0.25 to 1.0 M sodium chloride all in 0.025 M sodium phosphate at pH 7.0±0.1. Chondroitinase B elutes in the 0.25 M sodium chloride step while chondroitinase AC elutes at 0.85 to 0.95 M sodium chloride. The chondroitinase B fraction is diluted two-fold in 0.01 M sodium phosphate and applied to a strong cation exchange column (CBX-S, J. T. Baker, 1.6 cm i.d.×10 cm). The bound material is eluted at a flow rate of 1.0 cm·min$^{-1}$ with a linear gradient from 0.125 to 0.325 M sodium chloride in 0.025 M sodium phosphate at pH 7.0±0.1. Chondroitinase B elutes in a protein peak at 0.175 to 0.225 M sodium chloride and contains a minor contaminating protein of molecular weight 20,000 D. This protein is removed by gel filtration chromatography by loading the chondroitinase B sample onto a Superdex™ 200 column (1.0×30 cm, Pharmacia) and eluting with 0.05 M sodium phosphate, pH 7.2 at a linear flow rate of 1.25 cm·min$^{-1}$ and collecting the protein containing fractions. The chondroitinase AC fraction collected from hydroxylapatite chromatography is diluted three-fold in 0.01 M sodium phosphate and applied to a strong cation exchange column (CBX-S, J. T. Baker, 1.6 cm i.d.×10 cm). The bound material is eluted at a flow rate of 1.0 cm·min$^{-1}$ with a linear gradient from 0.125 to 0.325 M sodium chloride in 0.025 M sodium phosphate at pH 7.0±0.1. Chondroitinase AC elutes in a single protein peak at 0.175–0.225 M sodium chloride. Purification results for the chondroitinase enzymes are shown in Table 2.

TABLE 2

Purification of chondroitinase enzymes from *Flavobacterium heparinum* fermentations

| sample | activity (IU) | specific activity (IU/mg) | yield (%) |
|---|---|---|---|
| fermentation | | | |
| chondroitinase AC | 65,348 | 0.764 | 100 |
| chondroitinase B | 21,531 | 0.252 | 100 |
| osmolate | | | |
| chondroitinase AC | 39,468 | 1.44 | 60 |
| chondroitinase B | 15,251 | 0.588 | 71 |
| cation exchange | | | |
| chondroitinase AC | 27,935 | 9.58 | 43 |
| chondroitinase B | 13,801 | 4.731 | 64 |
| cellufine suifate | | | |
| chondroitinase AC | 18,160 | 22.6 | 28 |
| chondroitinase B | 6,274 | 21.2 | 29 |
| hydroxylapatite | | | |
| chondroitinase AC | 14,494 | 146.8 | 22 |
| chondroitinase B | 3,960 | 65.62 | 18 |
| strong cation exchange | | | |
| chondroitinase AC | 9,843 | 211.4 | 15 |
| chondroitinase B | 4,104 | 167.2. | 18 |
| gel filtration | | | |
| chondroitinase B | 2,814 | 278.7 | 13 |

Isolation of Recombinant Enzymes.

Glycosaminoglycan degrading enzymes also can be isolated from recombinant expression systems such as the heparinase 1 expression system described by Sasisekharan, et al., *Proc. Natl. Acad. Sci. USA* 90:8660–8664, 1993; the heparinase II and III expression systems disclosed in U.S. patent application Ser. No. 08/258,639 "Nucleic Acid Sequences and Expression Systems for Heparinase II and Heparinase III Derived From *Flavobacterium heparinum*" by Su, et al., filed Jun. 10, 1994; or the chondroitinase AC and B expression systems disclosed in U.S. patent application Ser. No. (B258000677US) "Chondroitin Lyase Enzymes" by Bennett, et al., filed Jul. 8, 1994, the teachings of which are incorporated herein. In these expression systems, the *F. heparinum* genes are isolated and cloned into plasmids downstream from an inducable promoter. The plasmids are introduced into *E. coli* and the expression of the desired enzyme directed by a suitable induction method such as temperature shift and addition of IPTG to the medium.

The enzymes can be recovered in a purified form by a modification of the methods described herein. Cell disruption is achieved by homogenization, sonication or enzyatic treatment to break the cell wall and release cytoplasmic components. If enzyme synthesis results in aggregation, the aggregate can then be dissolved by a denaturing agent, 3 to 6 M guanidine HCl or 4 to 8 M urea and the protein refolded by removal of the denaturing agent through dialysis or dilution. The refolded enzyme can be further purified using the liquid chromatographic methods described above.

Construction of Fusion Proteins

Fusion proteins incorporating glycosaminoglycan degrading enzymes ligated to proteins with specific binding properties can be created by recombinant molecular biology techniques. By choosing an appropriate binding protein, the glycosaminoglycan degrading activity can be targeted to specific sites in vivo. For example, epidermal growth factor binds cell receptors expressed preferentially on the surface of smooth muscle cells as described by Pickering, et al., *J Clin Invest*, 91:724–729, 1993. Fusion proteins containing this moiety ligated to a heparinase protein direct heparin or heparan sulfate degrading activity to the surface of smooth muscle cells, thereby diminishing their response to available cytokines. This type of fusion protein is of value in combating disease states that result from overgrowth of smooth muscle cells such as the vascular conditions of atherosclerosis and re-occlusion of vessels following percutaneous transluminal coronary angioplasty.

Heparinase fusion proteins created by genetic engineering retain the binding and catalytic properties of heparinase and of the protein to which it is fused. For example, the gene for heparinase 1 was isolated from *F. heparinum* as described by Sasisekharan, et al., *Proc. Natl. Acad. Sci.* 90:3660–3664, 1993, and an Eco R1 restriction site was inserted 5' to the codon encoding the glutamine-21 residue by polymerase chain reaction. A fragment containing the heparinase 1 gene was prepared by digestion with restriction endonucleases; Eco R1 and Bam H1, and ligated to the Eco R1/Bam H1 cleaved pMALc2 plasmid (New England Biolabs). The resulting plasmid contained a hybrid gene encoding a 82,000–85,000 protein incorporating the maltose binding protein (MalB) fused 5' to the heparinase 1 gene. This plasmid was inserted into *Esherichia coli* HB101 cells using the calcium chloride mediated method described by Cohen et al., *Proc. Natl. Acad. Sci.* 69:2110–211. These cells exhibited heparinase activity under the control of the lac promoter, allowing synthesis of the fusion protein by addition of 0.1 mM of the inducing agent IPTG to the growth medium.

The HB101(pMALc2-HEP1Q21) cells were grown to a cell density of 1.0 g/L dry cell weight in 500 ml, M9 medium containing 0.1 mM IPTG at 37° C. and concentrated by centrifugation, 10,000 g×10 minutes. The cell pellet was suspended in 10 ml 0.025 M Tris, pH 7.7, and the cells disrupted by sonication using a Heat Systems Model XL2020, 4.5 minutes, power level 3, 30 second on 30 second off cycles. Cell debris was removed by centrifugation, 10,000 g×10 minutes, and the supernatant applied to an amylose affinity resin column (1.0 i.d.×2 cm, New England Biolabs). The bound protein was eluted with a step gradient of 0.025 M Tris containing 0.01 M maltose at pH 7.5. The fusion protein eluted in a protein peak which displayed a heparinase specific activity of 23.77 IU/mg.

The heparinase-maltose binding fusion protein also can be purified by standard protein separation techniques based on heparinase properties. Cell sonicates were fractionated by ammonium sulfate precipitation. Non-specific proteins were removed with a precipitation step at 1.7 M ammonium sulfate and the supernatant precipitated by raising the ammonium sulfate concentration to 3.2 M. The precipitated material contained the fusion protein and was resuspended in 0.025 M sodium phosphate, pH 6.5. The material was applied to a weak cation exchange column (1.6 i.d.×10 cm, CBX, J. T. Baker) and eluted with sequential step gradients of 0.0 M sodium chloride, 0.01 M sodium chloride, 0.25 M sodium chloride and 1.0 M sodium chloride, all in 0.025 M sodium phosphate. The fusion protein eluted in the 0.25 M sodium chloride elution fraction and displayed a heparinase specific activity of 29.95 IU/ml. These two purification procedures demonstrate that functional heparinase fusion proteins can be made by genetically linking a protein with desired binding properties to the N-terminal end of the heparinase protein and the resulting fusion protein retains the functionality of both heparinase and the protein to which it is fused. Examples of other targeting molecules which specifically bind to receptors such as ECM molecules include fibronectin, laminin, tenascin, thrombospondin, and collagens.

During the past two decades, the base knowledge of cell adhesion and migration in extracellular matrices (ECMs) at the molecular level has expanded rapidly. Early efforts in this area of research concentrated on the adhesion-promoting ECM protein fibronectin (FN). Sequence analyses and peptide mapping of the FN cell-binding domain yielded a minimal sequence which maintained cell-binding activity in the tetrapeptide Arg-Gly-Asp-Ser (RGDS). The biological interaction of the RGDS sequence with cell-surface fibronectin receptors was revealed by demonstrating that synthetic RGDS-containing peptides in solution could competitively inhibit fibroblast cell spreading on fibronectin-coated substrates. After the RGD cell adhesion recognition site in fibronectin was identified, the sequences of other cell adhesion proteins were examined for related signals. Other proteins known to carry functional RGD sequences include the platelet adhesion proteins fibrinogen and von Willebrand factor, osteopontin, and laminin. These findings imply that RGD is a ubiquitous cell adhesion signal. The use of fibronectin as the affinity ligand yielded a receptor that was a heterodimer with a 160 kD $\alpha$-subunit and a 140 kD $\beta$-subunit. Similar affinity chromatography experiments have yielded distinct heterodimeric RGD-directed receptors specific for vitronectin and a platelet receptor with affinities for fibrinogen and fibronectin. These RGD receptors, known as integrins, have a heterodimeric structure characteristic of RGD-directed receptors, with $\alpha$-subunits ranging between 140 and 160 kD and $\beta$-subunits ranging between 90 and 140 kD. Integrins are characteristically membrane-spanning heterodimeric protein complexes consisting of an $\alpha$-subunit and a $\beta$-subunit. Integrin complexes containing $\beta_1$ and $\beta_3$ subunits generally are involved in cell adhesion to the extracellular matrix, while the $\beta_2$ integrins are involved in cell-cell adhesion.

Other binding proteins can be antibodies or antibody fragments that recognize specific cell markers, hormones or other molecules that are bound by cell surface receptors. An example of a hormone bound by certain cell types is estrogen, which is bound to a greater degree by certain types of cancer cells. Another example is melanin, which is also present in higher concentrations of certain cancer cells. Antibodies to many specific cell surface markers are known.

Protection of Proteins In Vivo

Methods for extending the in vivo half-life are known and routinely used, especially in the case of enzymes. Examples of suitable methods using attachment of polyethylene glycol moieties to the protein, which inhibits uptake by the reticuloendothelial system. Preparation and characterization of "peglyated" proteins is described by Lu, et al., *Pept. Res.* 6(3), 140–146, 1993; Delgado, et al., *Critical Rev. Ther. Drug Carrier Syst.* 9(3-4), 249–304, 1992, the teachings of which are incorporated herein.

Preparation of Pharmaceutical Compositions

The enzymes can be administered topically, locally or systemically. Topical or local administration is preferred for greater control. The enzymes, alone or in combination, are mixed with an appropriate pharmaceutical carrier, then administered in an effective amount to produce the desired effect on the treated cells using methods known to those skilled in the art, for example, for topical application, by direct application to a site, or for local application, by means of injection or catheter.

Targeting and effective concentration dosages can be achieved by preparation of targeted enzymes as described above, or by the use of targeting vehicles, such as a catheter or polymeric delivery system, to achieve controlled site specific delivery of enzyme.

Preparation of Heparinase Gels:

Glycosaminoglycan degrading enzymes can be mixed with a variety of common gels, creams or ointments to facilitate their application for treatment of dermal wounds. These gels or ointments can be administered alone or in a transdermal patch or bandage to facilitate penetration of an effective amount of enzyme to the cells which are to be treated.

Administration of Enzymes via Controlled Release Matrices or Injection:

Enzymes can also be formulated in a carrier for administration by injection, for example, in saline or an aqueous buffer, using standard methodology, or encapsulated in a polymeric matrix. Encapsulation of enzymes in controlled release formulations is well known; materials include but not limited to liposomes, lipospheres, biodegradable polymeric matrices, and vesicles. These encapsulants are typically microparticles having a diameter from 60 nm to 100 microns, but preferably less than ten microns, and more preferably one micron or less in diameter.

Proteosomes are prepared from outer membrane proteins of the Meningococcal bacteria and been reported to bind proteins containing hydrophobic anchors by Lowell, et al *Science*, 240:800 (1988). Proteosome proteins are highly hydrophobic, reflecting their role as transmembrane proteins and porins. When isolated, their hydrophobic protein-protein interactions cause them to form naturally multimolecular, membraneous 60 to 1000 nm vesicles or membrane vesicle fragments, depending on the strength of the detergent used in their isolation. The enzyme can also be encapsulated within a proteoliposome as described by Miller et al., *J. Exp. Med.* 176:1739–1744 (1992) and incorporated by reference herein, as described above with reference to proteosomes. Alternatively, the enzyme can be encapsulated in lipid vesicles such as Novasome™ lipid vesicles (Micro Vescular Systems, Inc., Nashua, N.H.). Another carrier is described in PCT US90/06590 by Nova Pharmaceuticals, the teachings of which are incorporated herein, which is referred to as a liposphere, having a solid core and an outer shell layer formed of phospholipid.

The carrier may also be a polymeric delayed release system. Biodegradable synthetic polymers are particularly useful to effect the controlled release of enzymes. Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals is poly (d,l-lactide-co-glycolide) (PLGA). This is a biodegradable polyester that has a long history of medical use in erodible sutures, bone plates and other temporary prostheses, where it has not exhibited any toxicity. A wide variety of pharmaceuticals including peptides and antigens have been formulated into PLGA microcapsules. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction. Other means for encapsulation include spray drying, co-precipitation, and solvent extraction.

Enzymes can also be applied as films or implants, for example, to coat a tissue where growth is to be inhibited. Examples of materials used for controlled release which are administered as gels or films incorporating the agent to be released include Pluronics™ (BASF), copolymers of polyethylene oxide and polypropylene glycol.

Means for Administration

The enzymes can be administered topically, as described above, or by injection. Typically, injection is performed using either a syringe or catheter. The advantage of the catheter is that material can be applied to surfaces such as the inside of blood vessels during a procedure such as angioplasty, where the goal is to inhibit restenosis by inhibiting the abnormal proliferation of cells that frequently follows the surgical procedure. Enzymes can also be administered simultaneously with surgery, so that healing of the wound is enhanced. Enzymes could also be admnistered during surgery to accelerate healing of the surgical wound. This could be accomplished by formulating the enzyme in a biocompatible gel or salve that would be applied directly to the wound site at the conclusion of the corrective procedure.

Glycosaminoglycan degrading enzymes can be applied intra-dermally to elicit an accelerated formation of new vessels in ischemic regions. Mechanistically, this is achieved by the dislodgment of growth factors from their extracellular storage reservoir where they are sequestered by heparan sulfate proteoglycans and by enhancing the mobility of cytokines and chemoattractants through the diseased tissue area.

The present invention will be further understood by reference to the following non-limiting examples.

EXAMPLE 1

Preparation of Topical Enzyme Compositions.

A 0.5 ml solution of 0.01 M sodium phosphate 0.4 M sodium chloride and 200 IU heparinase 1, purified as described herein, was mixed with either 9.5 ml gel consisting of 1% carboxymethyl cellulose (Sigma), 40% USP glycerol and Nanaopure™ water or 9.5 ml of a carbomer based gel (carbomer™ 950, Keystone Laboratories).

A portion of each mixture was analyzed for heparinase activity using the spectrophotometric method described by Yang, et al., *J. Biol Chem.* 260(3):1849–1857, 1985. A modification of the agarose plate assay system for monitoring heparin degradation described by Zimmermann, et al. *Appl Environ. Microbiol*, 56(11):3593–3594, 1990, was incorporated to monitor the desorption of heparinase from various carriers. A solution containing 0.5% USP sodium heparin (Celsus Laboratories) and 1.0% purified agarose (Bio-Rad) in 0.25 M sodium acetate and 0.0025 M cacium acetate at pH; 7.0±0.5, was mixed at 95–100° C., cooled to 45–60° C., poured in 3 ml portions into 5 ml plastic disposable cuvettes and allowed to solidify by cooling to room temperature. Heparinase solutions (0.5 ml, 20 IU/ml) and heparinase containing gels (0.3–0.7 ml) were applied to the top of the heparin/agarose gels and incubated at 37° C. for 1 h. The heparinase formulations were discarded, a cylindrical cross section of the gels removed with a glass Pasteur pipet and the cylinders placed in a 2% protamine sulfate solution (Sigma). After 4–12 h, a heparin-protamine precipitation was observed as an opaque white substance. The extent of heparinase desorption was determined by the depth of the clear zone located at the top of the excised cylindrical gels.

This experiment was repeated in the carboxymethyl cellulose/glycerol formulation using either 20 IU/ml chondroitinasese AC or 20 IU/ml chondroitinase B as the active ingredient and chondroitin sulfate A or dermatan sufate B as the test reagent. The results are shown in Table 3.

TABLE 3

Enzymatic activity and desorption of heparinase 1 from pharmaceutical gel formulations.

| pharmaceutical | | activity | desorption (mm) | |
|---|---|---|---|---|
| carrier | enzyme | (IU/ml) | 1 hour | 4 hour |
| PBS | heparinase 1 | 100 | 4 | ND |
| 4% polyethylene oxide | heparinase 1 | 6.9 | 3 | ND |
| carbomer gel | heparinase 1 | 5.5 | 1 | ND |
| glycerol/CM cellulose | heparinase 1 | 12.2 | 3 | 7 |
| PBS | chondroitinase AC | 16.4 | 3 | ND |
| glycerol/CM cellulose | chondroitinase AC | 12.5 | 1 | 3 |
| PBS | chondroitinase B | 4.7 | 3 | ND |
| glycerol/CM cellulose | chondroitinase B | 6.5 | 1 | 4 |

EXAMPLE 2

Preparation of a Heparinase or Chondroitinase Bandage.

The three bacterial heparinases and two chondroitinases, purified as described herein, were placed in solutions containing 0.01 M sodium phosphate, 0.2 M sodium chloride, pH 7.0 and 35 IU/ml enzyme. Semi-solid gels consisting of 4% polyethylene oxide (7.5 cm×5 cm×0.3 cm) were contacted with 6 ml enzyme solution for 3 h, during which time more than 70% of the enzyme solution absorbed into the gel matrix.

Figure 1A:
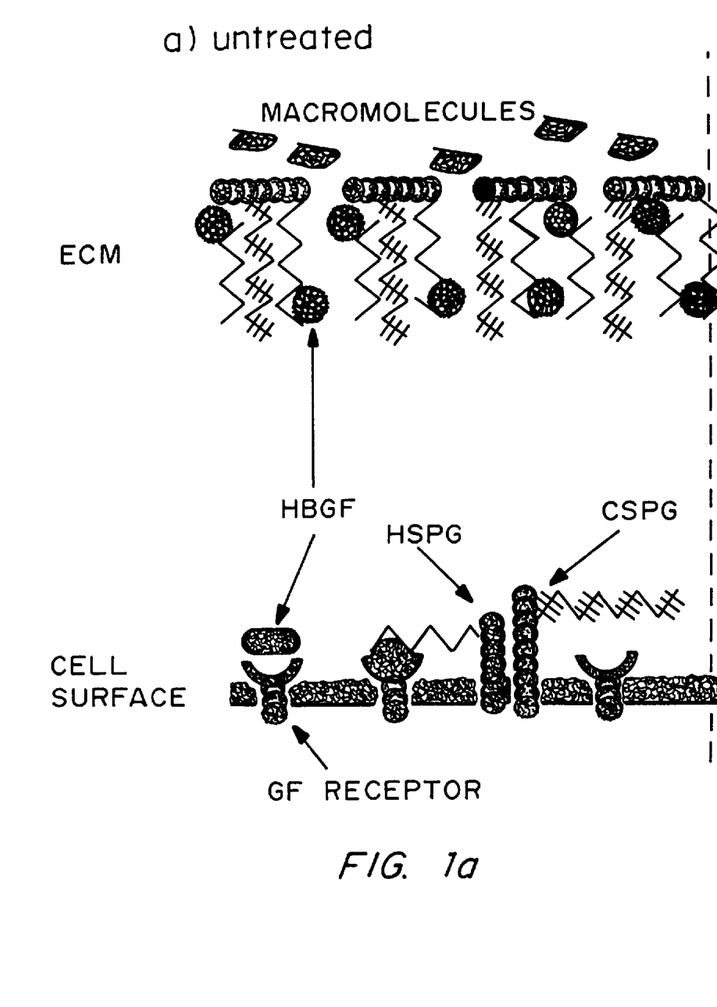
Figure 1B:
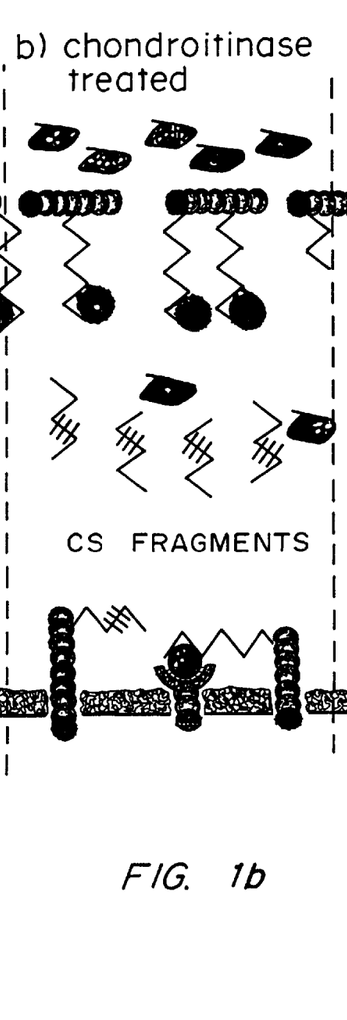
Figure 1C:
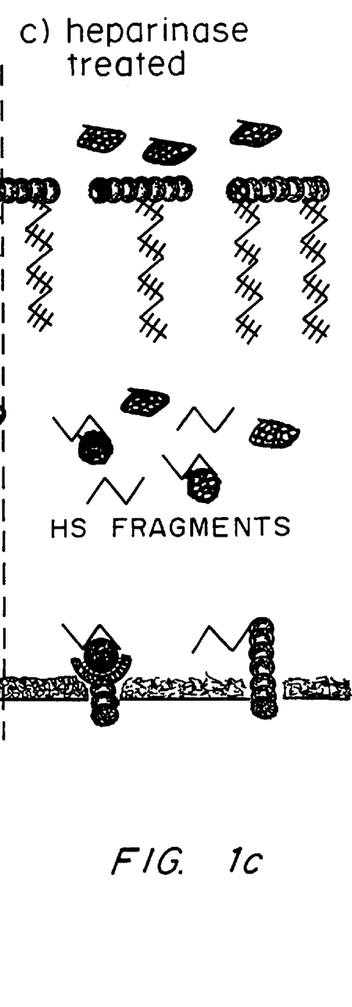
Figure 2:
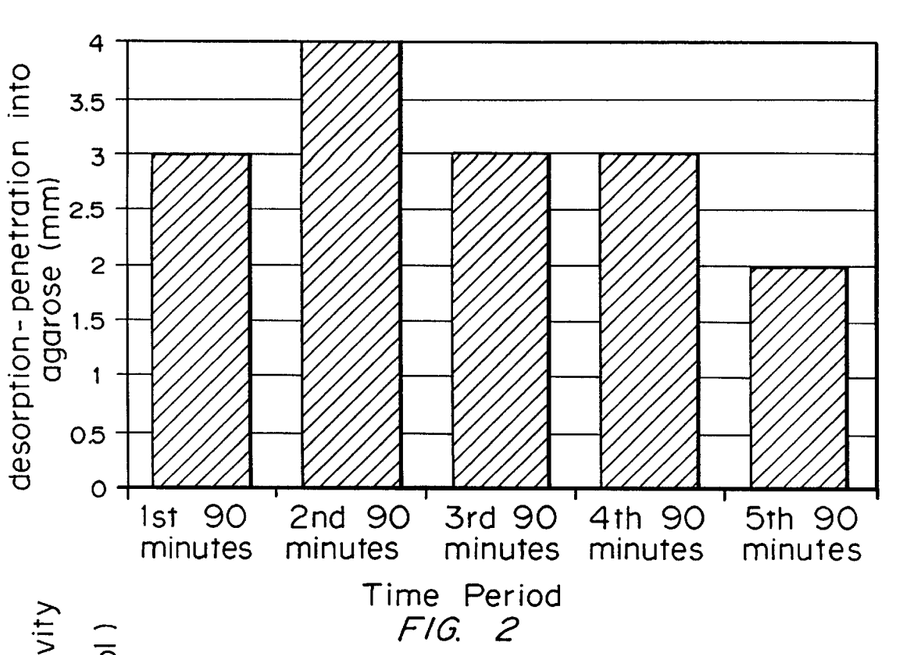

The enzyme containing gels were then tested for bioavailability (desorption) by the protamine precipitation of glycosaminoglycan—agarose gels as described herein. Enzyme containing patches were allowed to absorb to glycosaminoglycan-agarose gels for 90 minutes at 37° C. before being transferred to a fresh agarose gel. The procedure was repeated for a total period of 7.5 hours. Semi-solid gels consisting of 4% polyethylene oxide (7.55×0.3 cm) were soaked in 6 to 8 ml heparinase 1 at a concentration of between 35 and 60 IU/ml for three hours during which time the enzyme was absorbed into the matrix. The matrices were applied to 1% agarose gels containing 0.05% heparin and incubated at 37° C. Enzyme containing gels were transferred to fresh agarose gels each 90 minutes for a total of 7.5 hours. After incubation the agarose gels were contacted with 2.0% protamine sulfate to precipitate unfractionated glycosaminoglycan. Penetration of the enzymes was observed by measuring the depth of the clear zone in the precipitated agarose gels. The results are illustrated in FIG. 2.

EXAMPLE 3
Release of Growth Promoting Activity from Extracellular Matrix

Flavobacterial heparin degrading enzymes can dislodge substances exhibiting growth promoting activities from extracellular matrices. Primary endothelial cells were isolated from bovine corneal tissue and maintained in DMEM containing; 10% fetal calf serum, and 5% calf serum. Cells from confluent petri dishes were diluted 10-fold and grown in DMEM containing 10% fetal calf serum, 4% dextran and 5% calf serum, in 96-well plates for 12 to 14 days and were supplemented with FGF-2 at the rate of 0.5 ng/ml-day. The endothelial cells were removed by treatment with a solution containing 0.5% Triton and 0.02 M sodium hydroxide in phosphate buffered saline for 0.5 to 5 minutes, followed by three washes with phosphate buffered saline. This procedure yields plates coated with a layer of extracellular matrix which is stable for two years when stored at 4° C. in phosphate buffered saline.

Varying amounts of the glycosaminoglycan degrading enzymes, purified as described herein, were added to the extracellular matrix in 0.2 ml/well containing 0.16% fetal calf serum—DMEM. Contacting with the glycosaminoglycan degrading enzymes was allowed to take place for 1 hour at 37° C. The supernatants from these enzyme-extracellular matrix reaction mixtures were then tested for mitogenic activity by determining the incorporation of $^3$H-thymidine by quiescent balb/c 3T3 fibroblasts as described by Vlodavsky et al., *Proc. Natl. Acad. Sci.* 84:2292–2296, 1987.

Figure 3:
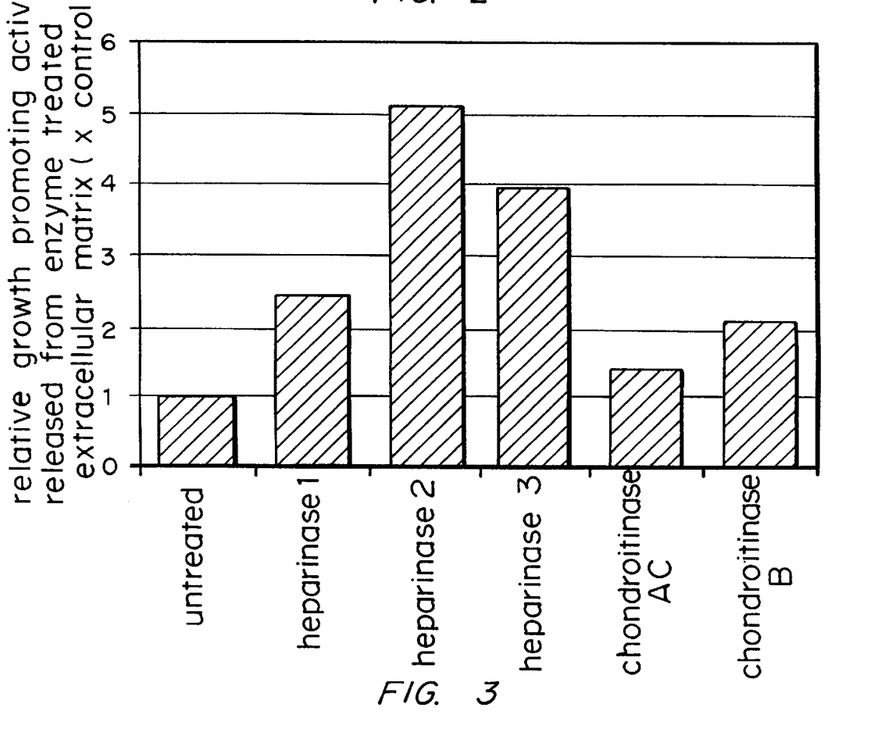

Extracellular matrices formed in vitro from a primary endothelial cell line were treated with either heparinase 1, 2 or 3 at a concentration of 0.1 IU/ml, chondroitinase AC at a concentration of 1.0 IU/ml or chondroitinase B at a concentration of 0.5 IU/ml for 60 minutes. Reaction supernatants were tested for the presence of mitogenic activity by a thymidine incorporation assay. The results are shown in FIG. 3.

EXAMPLE 4
Keparin and Heparan Sulfate Degrading Enzymes can also be Used to Release Growth Promoting Activity from Intact Animal Tissues.

Bovine corneas were harvested from cows at the time of slaughter. Each cornea was dissected into two equal sections and each section placed in 0.4 ml, DMEM. Heparinase at 0.1 IU/ml was added to one of the corneal sections and incubated at 37° C. for 20 minutes. The remaining section from the same cornea served as the control. 20 μl aliquots from each reaction were transferred to 96-well plates containing starved 3T3 fibroblasts in a total volume of 200 μl in DMEM containing 0.2% fetal calf serum. $^3$H-thymidine was added to each well and the cells incubated for 48 hours at 37° C.

Figure 4:
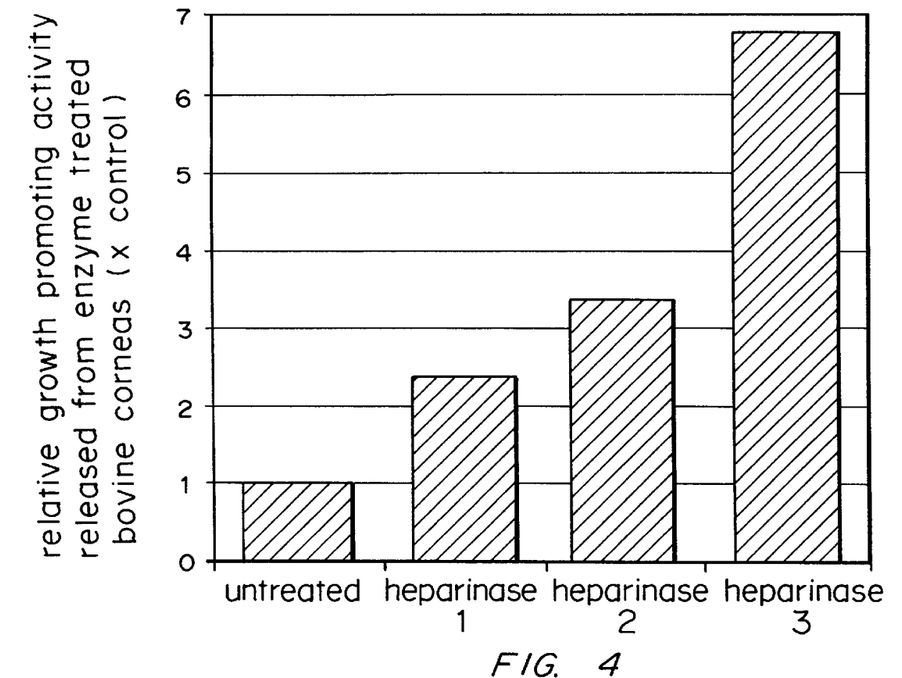

Bovine corneas were harvested, dissected into two equal portions and treated with either heparinase 1, 2 or 3 at a concentration of 0.1 IU/ml. Reaction supernatants were tested for the presence of mitogenic activity by incorporation of $^3$H-thymidine determined by the method of Vlodavsky, et al. The results are shown in FIG. 4.

EXAMPLE 5
Treatment of Extracellular Matrix by Glycosaminoglycan Lyases.

Glycosaminoglycan degrading enzymes alter the extracellular matrix by cleaving the glycosaminoglycan components of the extracellular matrix proteoglycan. Preparation of extracellular matrix with $^{35}$S-sulfate containing proteoglycan and subsequent digestion of this radiolabelled matrix with Flavobacterial glycosaminoglycan degrading enzymes allows a quantitative assessment of the effect of the enzymes. $^{35}$S-sulfate containing extracellular matrix was produced by seeding dishes with primary bovine corneal endothelial cells grown to confluence in DMEM with 10% fetal calf serum and 5% calf serum diluted 10-fold into Fisher medium supplemented with 10% fetal calf serum, 5% calf serum, 4% dextran, and 25 μCi/ml Na$_2$$^{35}$SO$_4$ and cultured for 12 to 14 days with the addition of 0.5 ng/ml-day FGF-2. The endothelial cells were removed from the radiolabelled extracellular matrix by treatment with a solution containing 0.5% Triton, 0.02 M sodium hydroxide in phosphate buffered saline for 0.5 to 5 minutes, followed by three washes with phosphate buffered saline.

Figure 5:
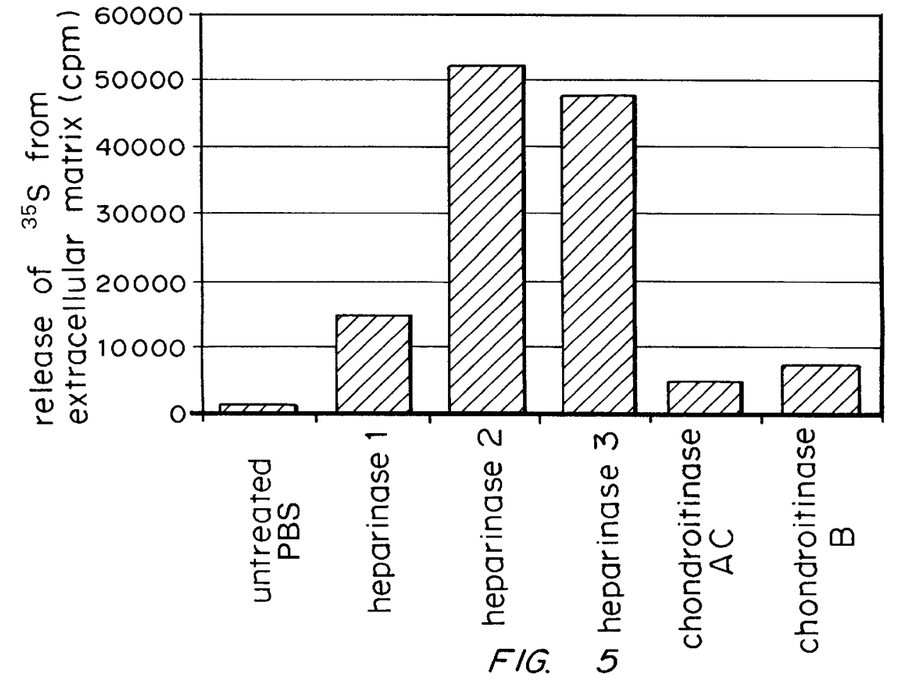

Extracellular matrix containing $^{35}$S sulfate in the glycosaminoglycan portion was treated with phosphate buffered saline or heparinases 1, 2 or 3, or chondroitinases AC or B at a concentration of 0.1 IU/ml in 1 ml/well dishes containing phosphate buffered saline, and the digestion was allowed to proceed for 1 hour at 37° C. The amount of glycosaminoglycan released was determined by measuring the radiolabelled sulfate released to the supernatant with a Packard 1600 TR liquid scintillation counter. An estimate of 80,000 cpm was the total amount of radiolabelled sulfate contained in each reaction. The results are shown in FIG. 5.

The action of the Flavobacterial heparin degrading enzymes is extremely rapid, and the generation of $^{35}$S-sulfate labeled material occurs seconds after their addition to radiolabelled extracellular matrix as described above. In contrast, an equal amount of mammalian heparanase isolated from human placenta shows a 15 to 20 minute lag time after addition to the radiolabelled matrix before any measurable increase in the level of soluble $^{35}$S-sulfate labeled material is detected. This observation further differentiates the mammalian and bacterial enzymes.

While treatment of the extracellular matrix with glycosaminoglycan degrading enzymes alters the glycosaminoglycan component of the extracellular matrix proteoglycan, the overall structural integrity of the matrix remains unchanged as viewed by electron microscopy. Although structurally intact, enzymatically treated extracellular matrix exhibits enhanced permeability to macromolecules. This increased permeability can be demonstrated by examining the ability of the Flavobacterial glycosaminoglycan degrading enzymes to facilitate the passage of 25 nucleotide bases up to 2 Kb nucleotide fragments across a 0.45 micron pore polyethylene terephthalate (PET) membrane coated with extracellular matrix. Primary bovine corneal endothelial cells maintained as described above are diluted 1:10 from confluent dishes and seeded onto 0.45 micron pore PET membrane tissue culture inserts (Falcon) in DMEM supplemented with 10% fetal calf serum, 5% calf serum, 4% dextran, and cultured for 12 to 14 days with the addition of 0.5 ng/ml-day FGF-2. The endothelial cells are removed as described above, and the extracellular matrix coated PET inserts treated with either heparinase 1, 2, or 3 at a concentration 0.1 IU/ml, or with either chondroitinase AC or B at a concentration of 1 IU/ml in phosphate buffered saline at 37° C. for 1 hour and rinsed three times with phosphate buffered saline.

The enzymatically treated extracellular matrix coated PET inserts, along with an untreated extracellular matrix coated PET insert and an uncoated PET insert, are placed into 12 well dishes and 2 ml of phosphate buffered saline added to each well. Radiolabelled macromolecules are added inside each PET insert, and 100 μl aliquots of phosphate buffered saline solution in the well surrounding the PET insert taken after a 15 minute incubation at 37° C.

Aliquots are assayed for $^{32}$P-containing material by liquid scintillation in a Packard 1600 TR scintillation counter.

EXAMPLE 6

Treatment of Cell Surface with Glycosaminoglycan Lyases.

Glycosaminoglycan degrading enzymes can attenuate a cell's response to growth factors by cleaving the glycosaminoglycan component of cell surface proteoglycans. Vascular smooth muscle cells were grown in 96 well plates in DMEM supplemented with 10% fetal serum until confluent. The cells were treated with either heparinase 1, 2 or 3 or chondroitinase AC at a concentration of 0.1 IU/ml for 1 hour at 37° C., then chilled on ice and washed twice with an incubation medium comprised of 0.025 M HEPES, 0.002 M Tris and 0.1% BSA in DMEM at pH 7.5. The cells were suspended in 0.25 ml incubation buffer containing 5 ng $^{125}$I-FGF-2 (0.5 µCi) and incubated at 4° C. for 2 hours. Adsorption of FGF-2 to cell surface glycosaminoglycan was determined by washing the cells with an elution buffer consisting of 0.025 M HEPES and 2 M sodium chloride at pH 7.4, and measuring the recovered $^{125}$I with a gamma-counter (Wallac, Model 1740).

Figure 6:
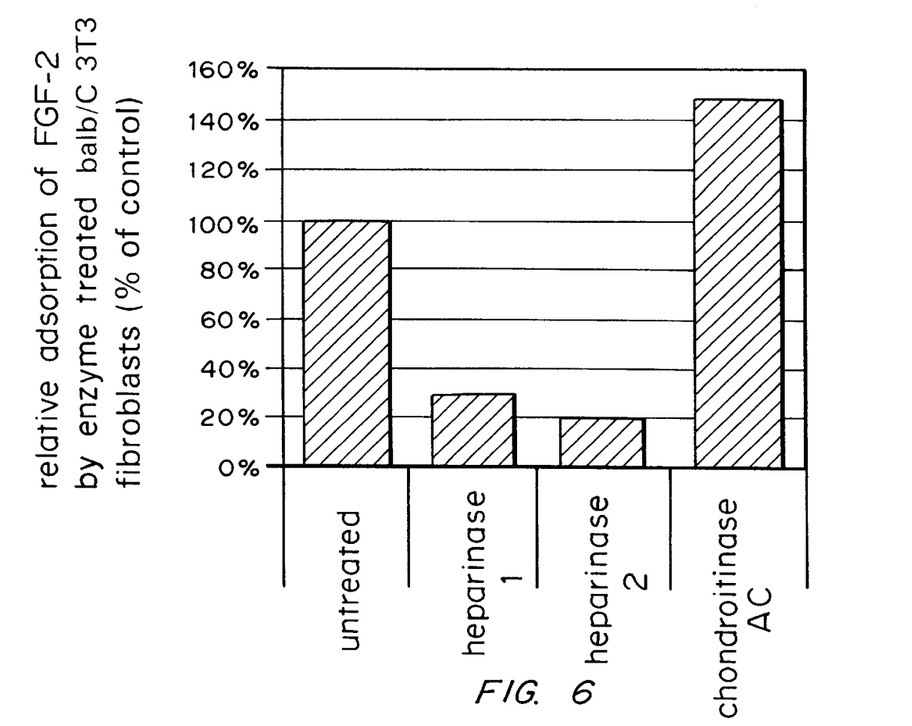

Balb/C 3T3 fibroblasts were treated with 0.1 IU/ml heparinases 1, 2 or 3, or chondroitinase AC and exposed to $^{125}$I-FGF-2. The amount of FGF-2 adsorbed to the cell surface glycosaminoglycan was determined by extracting the glycosaminoglycan bound fraction in 0.025 M HEPES, 2.0 M sodium chloride and measuring FGF-2 using a gamma counter and is expressed as a percentage of FGF-2 bound to untreated cells. The results are shown in FIG. 6.

EXAMPLE 7

Control of Proliferation of Endothelial Cells using Glycosaminoglycan Treatment.

Glycosaminoglycan degrading enzyme treatment of cell surfaces can either enhance growth factor binding as in the case of chondroitin degrading enzymes, or inhibit growth factor binding as in the case of heparin and heparan sulfate degrading enzymes. The removal of cell surface heparan sulfate can be compensated by heparin or heparan sulfate fragments released from the extracellular matrix by enzymatic treatment.

Treated vascular smooth muscle cells were exposed to 0.1 IU/ml heparinase 2 at 37° C. for 20 minutes. Treated matrix was exposed to 0.1 IU/ml heparinase 2 at 37° C. for 20 minutes. After enzymatic treatment, the cells were washed with 0.1 ml PBS and exposed to 50 µl matrix supernatant.

Figure 7:
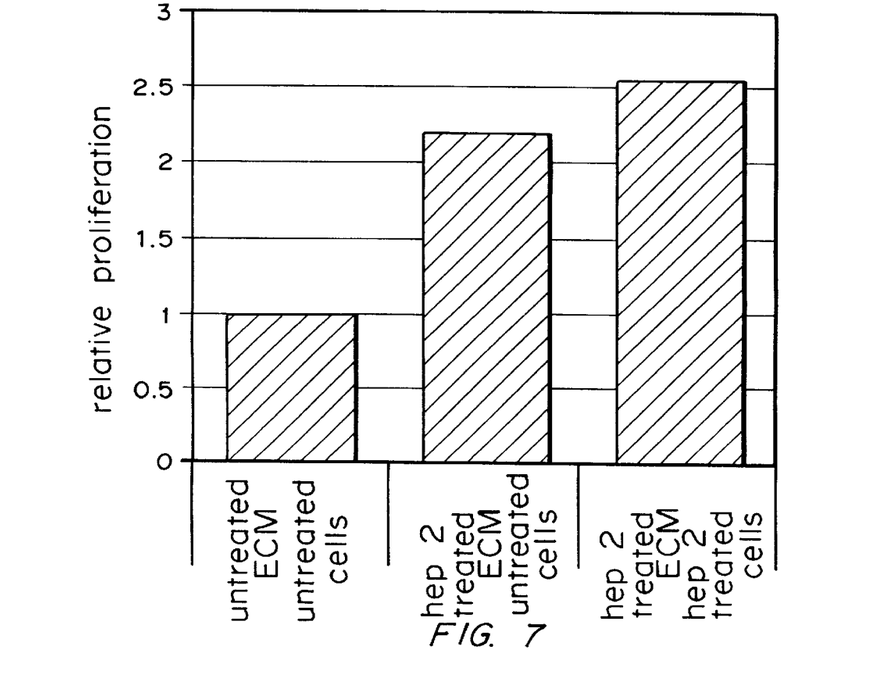

$^3$H-thymidine was included in the incubation and proliferation determined as described by Vlodavsky et al. Proliferation of vascular smooth muscle cells was monitored by thymidine incorporation and is expressed as a ratio of cells exposed to enzyme released material to that of untreated matrices for a) untreated ECM, untreated cells, b) heparinase 2 treated ECM, untreated cells, and c) heparinase 2 treated ECM, treated cells. The results are shown in FIG. 7.

The results show that if one separates cell matrix from cell surface, one will knock out receptor by treating the surface and release growth promoting activity by treating matrix, and that if one treats the matrix and the cell surface, growth promotion is observed since the matrix releases growth factor that compensates for the loss of heparin binding receptor.

EXAMPLE 8

Evaluation of Local Administration of Heparinase to Enhance Revascularization.

A rabbit hind limb ischemic model described by Pu, et al., *Circulation* 88:208–215, 1993, was used to evaluate the effectiveness of heparinase 1 on restoring vascularization. Three treatment groups were studied (N=4); saline control, FGF-2; 100 mg-day$^{-1}$ and heparinase 1; 100 IU-day$^{-1}$. Ischemia was surgically induced in the left hind limb and the compounds administered for 10 days beginning on the 11th day following surgery. Rates of vascularization were monitored by measuring the blood pressure in both limbs with a Doppler flowmeter and calculating the ratio of blood flow in the ischemic limb to that of the control (untreated limb).

Heparinase 1 and FGF-2 accelerated both the increase of blood pressure ratio as well as the extent of blood pressure ratio achieved 30 days post-treatment. At post-operative day 40, angiograms were performed to determine new vessel formation. The results are shown in Table 4.

TABLE 4

Treatment of ischemic hind limb

| agent | blood pressure ratio (IU/ml) | | | vessel formation |
|---|---|---|---|---|
| | day 10 | day 20 | day 30 | |
| PBS | 0.28 | 0.40 | 0.49 | 8.00 ± 1.00 |
| FGF-2 | 0.19 | 0.55 | 0.62 | 15.50 ± 2.38 |
| heparinase 1 | 0.30 | 0.60 | 0.71 | 22.50 ± 3.56 |

The data indicate the potential utility of compositions containing one or a combination of the *Flavobacterium heparinum* derived glycosaminoglycan degrading enzymes for accelerating tissue repair in humans.

Modifications and variations of the compositions and methods of use of the present invention will be obvious to those skilled in the art from the foregoing detailed description. Such modifications are intended to come within the scope of the appended claims.

We claim:

1. A method to enhance normal wound healing in a human or an animal comprising administering to the cells around the wound bacterial glycosaminoglycan degrading lyases selected from the group consisting of heparinase 2 from *Flavobacterium heparinum*, heparinase 3 from *Flavohacterium heparinum*, chondroitinase AC from *Flavobacterium heparinum*, and chondroitinase B from *Flavobacterium heparinum*, heparinase from Bacteroides strains, heparinase from Flavobacterium Hp206, heparinase from Cytophagia species, chondroitin sulfate degrading lyases from Bacteroides species, chondroitin sulfate degrading lyases from *Proteus vulgaris*, chondroitin sulfate degrading lyases from Microcossus, chondroitin sulfate degrading lyases from Vibrio species, chondroitin sulfate degrading lyases from *Arthrobacter aurescens*, and combinations thereof in an amount effective to enhance normal wound healing.

2. The method of claim 1 wherein the cells are contacted with an effective amount of a glycosaminoglycan degrading lyase to promote cell proliferation.

3. The method of claim 1 wherein the cells are contacted with an effective amount of a glycosaminoglycan degrading lyase to inhibit abnormal cell proliferation.

4. The method of claim 1 wherein the cells are selected from the group consisting of muscle cells, fibroblasts, endothelial cells and epithelial cells.

5. The method of claim 3 wherein the lyase is administered to a blood vessel in an amount effective to inhibit restenosis.

6. The method of claim 1 wherein the normal wound healing is accompanied by revascularization.

7. The method of claim 1 wherein the glycosaminoglycan degrading lyase is administered in combination with a delivery vehicle.

8. The method of claim 1 where the glycosaminoglycan degrading lyase is selected from the group consisting of heparinase 2 from *Flavobacterium heparinum*, heparinase 3 from *Flavobacterium heparinum*, and combinations thereof.

9. A pharmaceutical composition comprising a bacterial glycosaminoglycan degrading lyase selected from the group consisting of heparinase 2 from *Flavobacterium heparinum*, heparinase 3 from *Flavobacterium heparinum*, chondroitinase AC from *Flavobacterium heparinum*, and chondroitinase B from *Flavobacterium heparinum*, heparinase from Bacteroides strains, heparinase from Flavobacterium Hp206, heparinase from Cytophagia species, chondroitin sulfate degrading lyases from Bacteroides species, chondroitin sulfate degrading lyases from *Proteus vulgaris*, chondroitin sulfate degrading lyases from Micrococssus, chondroitin sulfate degrading lyases from Vibrio species, chondroitin sulfate degrading lyases from *Arthrobacter aurescens*, and combinations thereof in combination with a pharmaceutically acceptable carrier for localized administration of an effective amount to enhance normal wound healing.

10. The composition of claim 9 wherein the carrier is a pharmaceutically acceptable carrier for administration topically.

11. The composition of claim 9 wherein the carrier is selected from the group consisting of ointments, polymeric films, gels, microparticulates, microcapsules, liposomes, proteosomes, and lipospheres, implants, transdermal patches, and bandages.

12. The composition of claim 11 wherein the lyase is incorporated into a polymeric matrix.

13. A system for enhancing normal wound healing comprising
a purified naturally occurring bacterial glycosaminoglycan degrading lyase in combination with a pharmaceutically acceptable carrier and apparatus for delivery of lyases in combination with the carrier in a dosage effective to enhance normal wound healing.

14. The system of claim 13 wherein the apparatus for delivery is a catheter or endoscope.

15. A pharmaceutical composition comprising a bacterial glycosaminoglycan degrading lyase selected from the group consisting of heparinase 2 from *Flavobacterium heparinum*, heparinase 3 from *Flavobacterium heparinum*, chondroitinase AC from *Flavobacterium heparinum*, and chondroitinase B from *Flavobacterium heparinum*, in combination with a pharmaceutically acceptable carrier for localized administration of an effective amount to enhance normal wound healing, wherein the lyase is expressed from a recombinant nucleotide sequence in an organism in which it does not naturally occur and the lyase is processed differently than in the organism in which it naturally occurs.

16. The composition of claim 9 wherein the lyase is selected from the group consisting of heparinase 2 from *Flavobacterium heparinum*, heparinase 3 from *Flavobacterium heparinum*, and combinations thereof.

17. A pharmaceutical composition comprising a bacterial glycosaminoglycan degrading lyase selected from the group consisting of heparinase 2 from *Flavobacterium heparinum*, heparinase 3 from *Flavobacterium heparinum*, chondroitinase AC from *Flavobacterium heparinum*, and chondroitinase B from *Flavobacterium heparinum* in combination with a pharmaceutically acceptable carrier for localized administration of an effective amount to enhance normal wound heating, wherein the glycosaminoglycan degrading lyase is a fusion protein.

* * * * *